United States Patent [19]

Montgomery

[11] Patent Number: 5,743,686
[45] Date of Patent: Apr. 28, 1998

[54] PATTERN SIZING TOOL

[76] Inventor: Riley B. Montgomery, 784 N. 2525 West, West Point, Utah 84015

[21] Appl. No.: 747,251

[22] Filed: Nov. 18, 1996

[51] Int. Cl.⁶ ..................................... B23C 1/20
[52] U.S. Cl. .................... 409/181; 144/48.6; 144/154.5; 409/205; 409/211; 433/51; 433/223; 451/358
[58] Field of Search .................. 144/48.6, 154.5, 144/136.95; 409/175, 181, 182, 205, 211, 214, 218; 451/344, 358; 433/49, 51, 125, 163, 223

[56] References Cited

U.S. PATENT DOCUMENTS

| 578,588 | 3/1897 | Van Norman | 409/211 |
|---|---|---|---|
| 1,022,874 | 4/1912 | Riddell | 409/205 |
| 1,805,546 | 5/1931 | Howlett | 433/51 |
| 2,073,861 | 3/1937 | Wolf | 451/358 |
| 3,648,416 | 3/1972 | Rogers | 451/344 |
| 3,864,053 | 2/1975 | Harwood | 408/110 |
| 4,205,445 | 6/1980 | Tzeng | 433/51 |
| 4,941,826 | 7/1990 | Loran et al. | 433/51 |
| 5,150,993 | 9/1992 | Miller | 408/110 |

FOREIGN PATENT DOCUMENTS

| 2645733 | 10/1990 | France | 433/49 |
|---|---|---|---|
| 5996 | 4/1921 | Netherlands | 433/51 |

*Primary Examiner*—A. L. Pitts
*Assistant Examiner*—Christopher Kirkman
*Attorney, Agent, or Firm*—M. Reid Russell

[57] ABSTRACT

A pattern sizing tool for use as a milling device for removing a portion of a surface of a stiff material to leave a desired thickness of material and is particularly useful for milling a hard plastic coping like that produced in a tooth replacement procedure for forming, from that coping, a crown as a replacement tooth in a practice of a "lost wax casting procedure". The tool includes a pair of upper and lower arms that are coupled together at their ends to be scissored and are spring biased apart. The upper arm includes a mount with an arrangement for maintaining a dental rotary grinder thereon that has a chuck for mounting a milling burr. The milling burr has a surface opposite to an end of a footing that is maintained to extend from the lower arm whereby, when a dental technician manually moves the tool arms together the milling burr surface is moved towards the footing end whereon that technician has positioned a hard plastic coping, or the like, that is preferably formed from a light cure resinous material. The tool includes a stop to limit travel of the turning milling burr surface towards the footing end and is used by the technician to mill the coping to a desired wall thickness, by the technician manually moving the arms together, and repositioning the coping on the footing who repeats the process until the entire coping surface has been milled.

9 Claims, 2 Drawing Sheets

5,743,686

PATTERN SIZING TOOL

SPECIFICATION

BACKGROUND OF THE INVENTION

1. Field of the Invention

This invention relates to tools and tooling for use in dental technology procedures.

2. History of the Invention

The invention relates to dental technology tooling and specifically to milling devices for removing material off from a coping that is preferably formed by an application of a light cured resin in a liquid state onto a die that is representation of a crown preparation formed by a dentist in tooth replacement process, with the resin cured by light to form a hard wall coping that is milled utilizing the tooling of the invention to provide a coping having a uniform wall thickness that is then used in a lost wax casting procedure where the resin coping is reproduced as a metal coping that receives a ceramic material applied thereover to form a crown.

3. Prior Art

In a practice of dental technology for forming a crown, bridge or the like for installation, by a dentist, in a patient's mouth, the dentist supplies to the technician an impression of the patient's mouth. The technician pours a casting of a material such as plaster of paris, gypsum based material, or the like into that impression, with the case impression then removed. A die, that is a representation of a crown preparation formed by the dentist in the patient's mouth, is separated from the casting as by sawing that impression into sections. The die is then used for forming a coping that is removed from the die, with that coping, along with other copings, sprued to a tree that is fitted into a container known as a ring and receives a pour of impression material that hardens around the coping and tree. The ring is then heated to where the coping and tree "burn out" leaving a void in the hard impression material that the technician casts molten metal into, as by a spin casting technique known as lost wax casting. After the metal has hardened and cooled the impression material is broken away from the metal coping and tree and the coping is cut from the tree, with the tree salvaged for a next casting. The metal coping exterior and interior surfaces, as needed for fitting onto the die, are smoothed to receive a ceramic material built thereon. The ceramic coated metal coping is then fired in a furnace, as needed, until the technician has built up the ceramic material to a representation of a tooth that is for fitting onto the patient's preparation and cementing thereon by a dentist.

Heretofore as the term "lost wax" in the procedure known as "lost wax casting" implies, the coping formed on the cast impression die is a wax applied in a liquid state, by the technician, onto the impression coping surface until they deem the coping to have a proper shape and wall thickness. A determination of proper wall thickness has been done by eye, with a use of a caliper, or the like, the technician periodically lifting the wax coping off of the die and inspecting it as wax is added and shaved therefrom. As the wax is translucent, light will pass therethrough. The technician by looking through the wax can interpret, from the light passed therethrough the wall thickness to determine whether to add more wax or scrape wax off from the coping interior or exterior surfaces. Accordingly, achieving a proper or desirable coping wall thickness that is then translated into metal by a casting process has heretofore depended upon the skill and experience of the technician.

It has long been recognized that a use of wax as is suitable for forming a build up on a die, once removed from such die, that wax coping can be easily deformed as from exposure to heat, even the heat of the technician's hand, and may be deformed by being accidentally squeezed it, or the like, during the process of sprueing it onto a tree. Recently a use of a resinous material, such as a light cured resin, has been adapted for use for forming a plastic coping, replacing a wax coping. Such light cured resin is applied in a liquid state, as with a brush, with the technician exposing the build up to source light that the resinous material is sensitive to cure or harden it. Thereafter, the technician, using finishing tools, such as a motor turned rotary grinder, turns a grinder burr to remove materials from the coping to a desired wall thickness. Such removal of materials has, however, been a problem in that the cured plastic is opaque and therefore the technician has had to proceed careful so as not to cut through the coping. To prevent such occurrence, as the technician removes portions of the plastic coping surface, they have had to periodically check the amount of such material removal using, for example, a pair of calipers, or the like. Such surface material removal continues until the technician is satisfied with the coping that is then sprued, usually along with other copings, to a tree that is fitted in a ring that and receives the investment material for a practice of the lost wax casting procedure, as described above.

The present invention provides a tool that is held by the technician in their one hand with their other hand positioning the plastic coping on tool a footing. Thereafter, the technician, by squeezing together pivot connected arms of the tool, moves a platform maintained on one arm and whereon a rotary grinder, also known as a dental hand piece is maintained. The rotary grinder has an air or electric motor drive chuck that receives and mounts a burr stem therein, with the burr end moved towards the footing that extends for the other pivoting arm and whereon the plastic coping is maintained. The turning burr end surface engages the hard plastic coping surface, grinding materials therefrom at the point of contact. The tool of the invention provides for limiting the distance from the footing that the turning burr is allowed to travel to, establishing a desired coping wall thickness. When, the burr has ground the plastic coping surface at its point of engagement thereto, to a desired wall thickness, the technician releases pressure and the arms move apart under the urging of a spring bias, moving the turning burr away from the footing end, and allowing the technician to reposition the plastic coping on that footing end. Whereafter the technician reapplies pressure on the arms to again move the turning burr surface into contact the plastic coping surface and grind material therefrom to leave a desired wall thickness at that point or location. This procedure is repeated over the entire coping surface, including its apex area, producing a hard plastic coping that has a uniform wall thickness for use in a practice of a lost wax casting procedure. In a practice of which procedure, a metal coping that faithfully reproduces the size and shape of the hard plastic coping is formed. Also, it should be understood, the tool of the invention could also be used on cast metal copings or for other milling functions to size the wall or walls of a coping, or the like, formed from plastic, metal, pre-fired and post-fired ceramics, or the like, within the scope of this disclosure.

SUMMARY OF THE INVENTION

It is a principal object of the present invention in a pattern sizing tool to provide a hand operated device to be held by an operator who operates it to move pivot connected tool arms together, one of which arms mounts a rotary grinder turning a burr that engages a hard plastic coping surface maintained on the other arm, with the travel of the turning burr surface into engagement within the coping surface stopped at a set distance, grinding off the coping surface to leave a desired coping wall thickness.

Another object of the present invention in a pattern sizing tool is to provide a platform mount on one tool arm for maintaining the rotary grinder, and one such grinder is known as a dental hand piece that is preferably air driven but may be electric motor, or otherwise, driven to turn a chuck wherein a burr stem is fitted, with the other arm arranged as a footing mount that includes at least one and preferably a pair of pointed end footing posts, extending from a rotating turret for positioning to where the burr surface is above a footing pointed end, whereon a plastic coping is maintained by the technician to remove material therefrom with burr travel towards the coping surface limited by a stop.

Another object of the present invention in a pattern sizing tool is to provide a tool that a dental technician holds in their one hand while, with their other hand, they position a hard plastic coping on a footing pointed end, with, by the technician squeezing the tool pivotally connected arms together, a turning burr is moved into contact with a location on the surface of a plastic coping above the footing pointed end, which travel of the turning burr towards the footing pointed end is stopped at a set distance from that footing pointed end, at a desired coping wall thickness.

Still another object of the present invention in a pattern sizing tool is to provide a tool having pivotally connected opposing scissoring arms that are spring biased to spread apart and are arranged such that a dental technician can maintain the tool in their one hand and, with their other hand, can position a hard plastic coping on a pointed end of a footing that extends from a lower footing arm and where, by squeezing the arms together, a burr turning surface is moved into engagement with the coping surface, removing materials therefrom, to leave a coping with a desired wall thickness, which tool is efficiently operated to safely grind off, in turn, sections of the plastic coping surface to a desired wall thickness that is then reproduced as a metal coping in a practice of a lost wax casting procedure.

The pattern sizing tool of the invention includes a pair of arms that are pivotally connected at an end of each and includes a spring for spring biasing the arms unconnected ends, apart and further includes a stop for prohibiting movement together of the arms past a set distance. An upper arm includes a grinding tool mount that incorporates strapping, or the like, for maintaining a rotary grinder, such as a grinder known as a dental hand piece, that turns a chuck wherein a stem of a burr is maintained. The tool lower arm includes, on an end thereof at least one footing that is secured to extend from the arm end, and has a pointed end immediately opposite to the burr surface. The burr surface is moved towards the footing pointed end when the arms are pivoted together, with that movement opposed by the spring biasing. So arranged, the turning burr is moved towards the footing pointed end by the technician, using one hand, to squeeze the tool arms together. Arm travel together continues until a stop arranged between the arms is reached, limiting further burr travel towards the footing pointed end. The stop is preferably a set screw that is turned from one arm to engage a surface, such as a plate, on the other arm. Spaced markings are preferably scribed as a scale alongside the screw that including a reference indicator, or the like, that is for comparison with a scale marking for setting a spacing distance from the burr surface to the footing pointed end. In practice, the technician, holding a hard plastic coping on the footing pointed end, moves the burr surface into engagement with the coping, removing a portion of the coping surface above the pointed end. The coping, at that point, is milled to a wall of a desired thickness, with the procedure repeated until the entire coping surface has been milled to a desired wall thickness.

Preferably, the footing is one of at least a pair of footings that are secured at spaced intervals to extend from a pivoting turret that is maintained to rotate on the lower arm end. The technician turns the turret to move one or the other footing pointed end under the burr surface. To facilitate the technician moving the tool arms together, against the spring biasing, the lower arm includes a curved thumb rest that the technician hooks his thumb to and uses his index finger that rests on the body of the rotary grinder maintained on the upper arm tool mount to pivot the burr maintained in the rotary grinder chuck towards the footing pointed end. A hard plastic coping is held by the technicians in their other hand on the footing end as the burr is moved against the coping surface, removing materials therefrom. With the technician repositioning the coping, as needed on that footing end until the entire coping surface has been engaged by the burr surface, removing material therefrom until a desired coping wall thickness is achieved. Coping repositioning can involve turning of the turret to move, as needed, another footing arrangement under the burr surface to receiving the coping fitted thereon. Preferably, the turret includes two footings one of which is shorter than the other and is bent adjacent to its end into a right angle, for positioning the coping side on the pointed end, opposite to the burr surface. The longer footing is use in milling the footing apex or crown area. The finished plastic coping can be connected, along with other prepared copings, as desired, to a sprue, tree, or the like, and the assembly is fitted into a cylindrical container known in the industry as a ring, to receive a conventional investment material poured therein. After investment material hardening, the ring is placed in a furnace and the plastic coping and sprew, and the like, are burned out leaving their image in the investment material that then receives a molten dental metal, ceramic material, or the like, poured therein to reproduce the plastic coping. After separation, the coping is finished and can receive a ceramic dental material built up thereon into a crown, veneer, or the like, that hardens with firing in an oven for cementing by a dentist in a patient's mouth. Such finishing can, in fact, be accomplished utilizing the tool of the invention, used as set out above.

DESCRIPTION OF THE DRAWINGS

In the drawings that represent the best mode presently contemplated for carrying out the invention.

DETAILED DESCRIPTION

Figure 1:
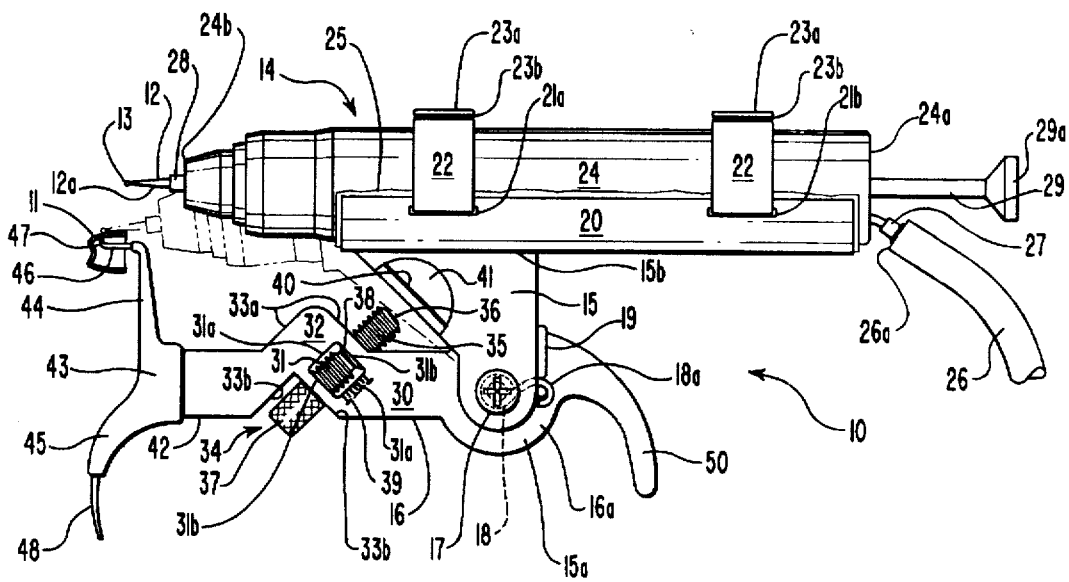
FIG. 1 is a side elevation view of a pattern sizing tool of the invention shown as including a pair of pivotally connected arms that are spring biased apart, with an upper arm shown as mounting a conventional dental rotary grinding tool that includes a chuck for receiving a stem of a dental burr fitted therein, and showing a lower arm as mounting a turret wherefrom a pair of spaced footings extend, each footing having a pointed end with a plastic coping shown maintained on one of the footing ends, with the tool shown as including a set screw type stop for limiting arm travel together, stopping burr surface travel at a set distance from the footing that is shown as bent adjacent to a pointed end, and showing in a broken lines the burr maintained in the rotary grinder having been moved towards the footing pointed end, milling a section therefrom.
Figure 2:
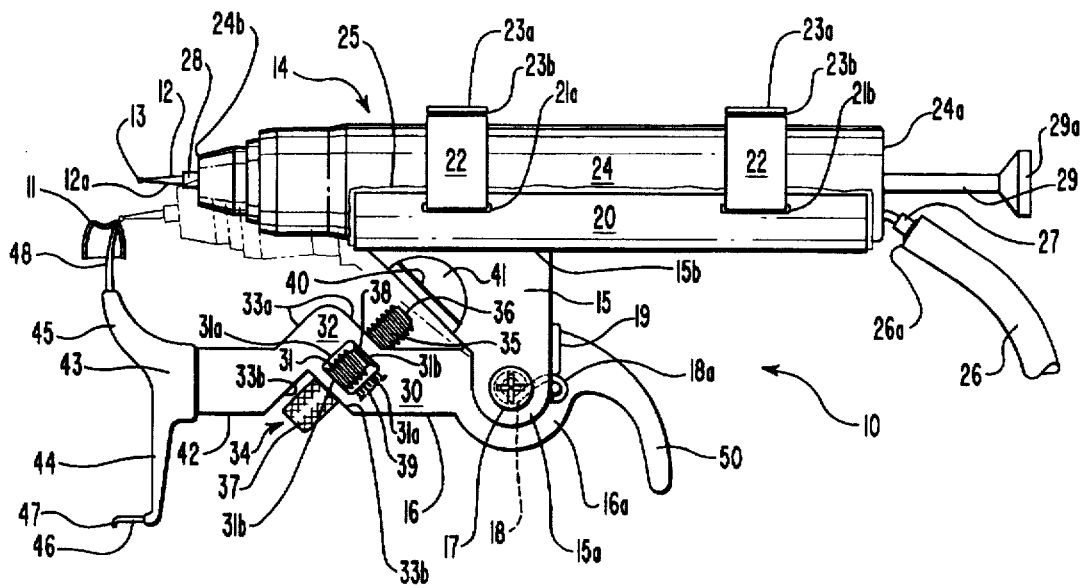
FIG. 2 is a view like FIG. 1 less the broken line portion and showing the footing turret as having been turned to align a pointed end of a straight footing with the burr surface and showing the coping maintained on the end of that straight footing.

FIGS. 1 and 2 shows a profile view of a pattern sizing tool 10 of the invention, hereinafter referred to as tool 10. The tool 10, as shown in broken lines in FIG. 1, is for milling a portion of an outer surface of a coping 11 by moving an outer cutting surface 13 of a burr 12 against the coping to mill off a section of that surface to a desired thickness. Whereafter, the coping is repositioned to mill another surface, and the process repeated until the entire coping surface has been milled to leave a desired wall thickness.

The coping 11 whose surface is milled by operation of tool 10 is preferably formed from a light cured resin, though the tool 10, can be used on a coping, or the like, formed from another material and can be used for a different use than that shown herein to include milling a metal coping surface, within the scope of this disclosure. A dental technician, using the tool 10 to mill a light cured resin coping 11, builds up the light cured resin in a liquid state on the surface of a die that is a representation of a crown preparation, or the like, as and has been formed by a dentist in a patient's mouth by removing an outer portion of a patient's tooth. Such crown preparation is reproduced as a negative image in a mold made by the dentist. A dental technician pours a plaster type material, in a liquid state, into that mold to form, when the plaster type material dries, a positive image of that crown preparation that should exactly reproduce the crown preparation. The positive image, not shown, is hereinafter referred to as a die, is separated, as by cutting it, as with a saw, from the mold, and is then prepared to receive a coping 11 built up thereon. In a manufacture of coping 11, for this invention, the technician coats the with a light cured resinous material, such as a Palavit GLC, manufactured by Kulzer Co. Though, it should be understood, a number of like resinous materials could be so used within the scope of this disclosure. The technician applies the resinous material, as with a brush, in a liquid state, painting the material into the die, by dipping the die, or the like, so as to coat the die to a thickness that is at least a desired wall thickness and greater of a finished coping. Such coping to be used in a lost wax coating process for manufacturing a metal coping to duplicate the plastic coping. Such metal coping to receive a ceramic material applied thereto for firing to form a crown, as set out below.

The technician applies the light cured resin over the die surface to a desired thickness as they determine will be equal to or greater than a desired wall thickness of a finished coping 11. The light cured resin can be cured in sections by an exposure to a light source that the resinous material is sensitive to and the coping is finally cured into a hard plastic by an exposure for a required period of time to such light source. The coping 11 is formed and cured into a hard plastic that is suitable to milling with a cutting tool, such as a dental burr 12, that is turned by a conventional rotary grinder 14. Such rotary grinder for the invention is used by a dentist drilling a patient's teeth, and by a dental technician forming a crown as a tooth replacement. A rotary grinder, commonly referred to in the industry as a "hand piece" known as a Model 220 Air Turbine Hand piece, manufactured by Buffalo Mfg., can be used as a preferred rotary grinder for use with the tool 10. It should, however, be understood, that any other rotary grinder as is suitable for inclusion with the tool 10, as described, or such other rotary grinder as the tool 10 can be modified for use with the invention, can be used with the invention.

The tool 10, as shown in the drawings, includes an upper arm 15 and a lower arm 16 that are joined together at their ends by a pivot coupling 17 that is formed through a lower arcuate end 15a of the upper arm 15, and a rear end portion 16a of the lower arm 16, as shown in FIGS. 1 and 2. The pivot coupling, as shown, is formed by a phillips head bolt that is fitted through aligned holes through the respective rear end portion 16 lower arcuate end 16a and upper arm 15 arcuate end 15a and, it should be understood, receives a nut, not shown, turned over a bolt threaded end and may include a lock washer, or the like, not shown. The pivot coupling 17, shown in FIGS. 1 and 2, preferably includes a spring 18, shown in broken lines as a sear spring, whose ends are, respectively, maintained to the upper arm 15, shown as end 18a, that rests against an end of a pier 19, and to the lower arm, not shown. The spring 18 provides for a spring biasing of the arms 15 and 16 to urge them apart to the attitude shown in FIG. 2. This spring biasing is overcome by the technician operating the tool 10, as set out below.

The upper arm 15, shown in the Figures includes a straight flat top edge 15b that is secured to a section of a longitudinal center axis of a cradle shaped tool mount 20. The tool mount 20 is shown to include a pair of aligned longitudinal slots 21a and 21b formed adjacent to opposing cradle edges that are spaced apart from one another. The slots 21a and 21b, respectively, are to each receive a strap 22 fitted therethrough with the strap ends 23a and 23b shown as including Velcro type fasteners that, when the straps are tightened across a cylindrical body 24 of the rotary grinder 14, are joined to hold the rotary grinder body 24 securely in the cradle 20, as shown. To further maintain the rotary grinder body 24 in the cradle 20, a section of a sheet of friction material 25 is preferably sandwiched therebetween.

The rotary grinder 14 is preferably a standard conventional grinder as is used by both dentists and dental technicians and is commonly referred to in the industry as a hand piece. The rotary grinder 14 is preferably air driven, illustrated by an air hose 26 having an end 26a that is fitted onto an end of an air fitting 27 that extends from the cylindrical body 24 rear end 24a. Air under pressure is passed through line 26 from a foot valve, not shown, that is operated by the technician. The rotary grinder 14 includes a chuck 28 journaled into a grinder body forward end 24b that is opened by a technician or dentist depressing a plunger 29 end 29a, shown extending outwardly from the rear end 24a. The plunger 29 is fitted through the chuck 28 to contact a straight stem end of a burr, drill or the like that has been positioned therein by the technician. The chuck 28 grips the burr stem and during turning. As shown, a stem end section 12a of the burr 12 is fitted into the chuck 28 with the burr then turned by operation of the rotary grinder 24.

The tool lower arm 16, includes a forward section 30 extending from the rear end portion 16a that is shown to include a rectangular opening 31 formed therethrough with the parallel long sides 31a thereof pointing at a contact plate 40 that is maintained in the upper arm 15, forming right angles thereto. As shown in the drawings FIGS. 1 through 3, the lower arm 16 includes section 32 having a dog leg bend formed therein back to its longitudinal axis providing an area between upper and lower sides thereof, 33a and 33b, respectively, wherethrough the rectangular opening 31 is formed. As shown, aligned holes are formed through parallel upper and lower sides 33a and 33b that pass through the center of parallel short sides 31b of the rectangular opening 31. The aligned holes are threaded to receive a threaded body of an adjustment screw 34 turned therethrough. The adjustment screw 34 preferably includes a threaded body 35, has an essentially flat top end 36 and includes a knob 37 at its opposite or lower end and receives a lock nut, not shown, turned over the opposite body 35 end, against the lower arm 16 surface. The knob 37 preferably includes a roughened or knurled surface to facilitate it being gripped by the technician. Additionally, a position marker 38, shown herein as a groove, is formed around the body 35, between flights of teeth. The position marker 38 is for alignment with one of a plurality of spaced number markings of a scale 39 that is scribed in the lower arm section 30 surface, alongside of a long side 31a of the rectangular opening 31. The scale 39 markings are preferably numbered with reference to the spaced markings that the technician aligns the adjustment screw position marking 38 to. So arranged, a selection of a particular numbered marking provides for setting a spacing distance between the burr surface 13 and a footing pointed end, as set out below. This spacing distance will be a wall thickness of coping 11 after its surface is milled off to that desired wall thickness using the tool 10.

Travel of the position marking groove 38 to align it with a specific scale 39 marking is, of course, provided by the technician turning the adjustment screw 34 knob 37. The adjustment screw flat top end 36 to engage when the upper and lower arms 15 and 16, respectively, the outer surface of contact plate 40 that is maintained or secured across an opening 41 formed in the upper arm 15. Contact of the adjustment screw 34 top end 36 with the contact plate 40 surface prohibits further travel of the burr end 13 towards a footing pointed end, as set out below.

Figure 3:
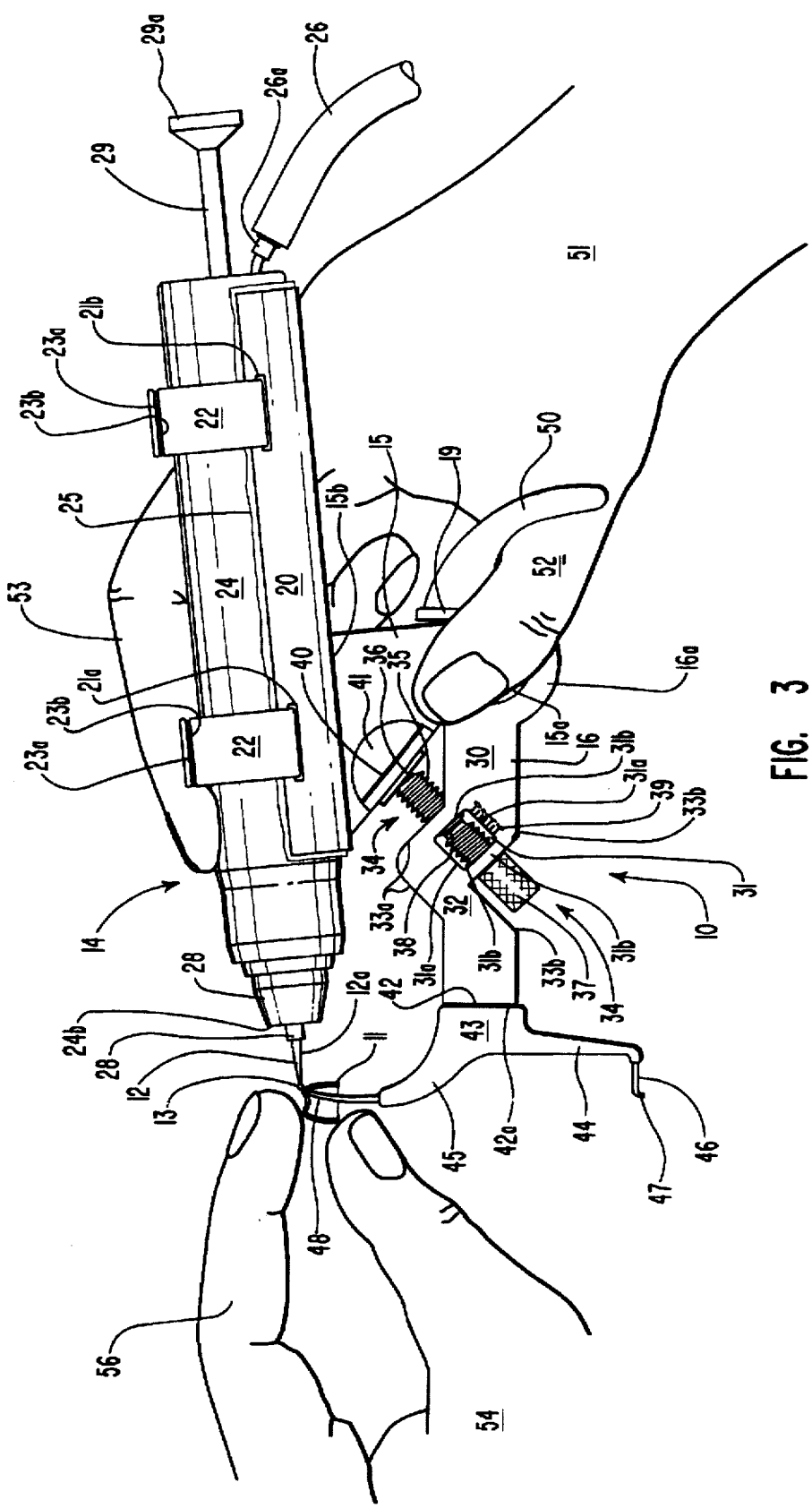
FIG. 3 shows a dental technician holding the invention of FIG. 2 in one hand and maintaining, with their other hand, a plastic coping on the pointed end of the footing, and, showing the technician's index finger used to pivot the tool upper arm, to move the burr surface into engagement with the plastic coping surface, and showing the set screw stop that extends from the lower arm with its end contacting a plate that is secured to the upper arm.

Shown in FIGS. 1 through 3, a turret 43 is journaled to turn across a flat forward end 42 of the lower arm 16 and includes, extending oppositely therefrom, a pair of footing arms 44 and 45. In FIG. 1 the footing arm 44 is shown to include a footing 46 that is bent adjacent to a top end 47, into a right angle and ends in a point. The coping 11, shown as a formed from a plastic, as shown, is supported on the footing 46 with the coping 11 outer surface, as shown in broken lines, in contact with the turning burr 12 outer end surface 13, milling materials therefrom until a set depth into the coping is reached. This milling process leaves a desired wall thickness of coping 11. With further burr travel towards the footing 46 bent top end 47 is stopped by contact of the adjustment screw 34 top end 36 with the surface of plate 40. FIGS. 2 and 3 show the turret 43 as having been turned or pivoted to align a pointed end of a straight footing 48 with the burr surface 13. Here, a coping 11 is shown maintained on the footing 48 pointed end for milling a section of the coping top surface when the burr end 13 is moved into contact therewith, as shown in broken lines. During the milling process, utilizing either the footing 46, that has the bent top end 47, or the straight tooting 48, the coping 11 is positioned onto the footing pointed end for milling, and is then repositioned thereon and milled against, and so on, until the entire coping 11 outer surface has been milled, leaving the coping wall and top areas with a desired or set coping thickness.

In a milling of coping 11, as set out above, and with respect to FIG. 3, the technician, holds the tool 10 in their one hand 51, fits a hook 50, that extends rearwardly from the lower arm 16, in the crook of their thumb 52, and positions their index finger 53 on top of the rotary grinder 14 cylindrical body 24. This index finger 53 is used to guide and control downward pivoting of the upper arm 15 to move the burr surface 13 towards the footing pointed end. Upon relaxation of pressure exerted through the index finger, the biasing of the spring 18 will return the upper and lower arms 15 and 16, respectively, to their spread apart attitude. During upper arm 15 travel, moving the turning burr surface 13 towards the coping 11, the technician controls the coping positioning by gripping it between the opposing surface of the thumb and forefinger 55 and 56, respectively, of their hand 54.

Hereinabove the tool 10 of the invention and its preferred use or uses by a dental technician, dentist, or the like, have been described for removing or milling off the surface of a hard plastic coping wall and top surface to a desired thickness. It should, however, be understood that the tool 10 may be utilized for other applications, as for example, milling a very hard wax or metal coping, a cast metal coping, or the like, within the scope of this disclosure.

It should accordingly be understood that, while a preferred embodiment of my invention in a pattern sizing tool has been shown and described herein, the present disclosure is made by way of example only and that variations and changes are possible without departing from the invention subject matter, and a reasonable equivalency thereof, coming within the scope of the following claims, which claims I regard as my invention.

I claim:

1. A pattern sizing tool comprising, a first arm and a second arm, each having first and second ends; pivot means for coupling said first and second arms so as to allow said second ends that are in opposition to one another to be moved apart and together; means for biasing said first and second arms apart; a rotary grinder means and means for maintaining it onto said first arm such that a milling end of said rotary grinder means is positioned apart from said second end of said second arm; a footing means extending from said second end of said second arm, which said footing means includes at least a pair of holder means each fitted to a positioning means that is for maintaining a coping thereon to be selectively positioned to where said coping is opposite to and spaced apart from said rotary grinder means milling end; and stop means arranged between said first and second arms for limiting movement together of said rotary grinder means milling end and an end of one said holder means.

2. A pattern sizing tool as recited in claim 1, wherein the arms are a first upper arm and a second lower arm; and the means for biasing is a spring for arrangement to said first upper and second lower arms to bias said arms apart.

3. A pattern sizing tool as recited in claim 2, wherein the means for maintaining the rotary grinder means to the first upper arm is a straight cradle that is arranged to support said rotary grinder means positioned therein, which said straight cradle is secured at its undersurface along its longitudinal axis to a straight top edge of said first upper arm; and a pair of strap means, that each include couplings formed on ends thereof, with each said strap means for arrangement with said straight cradle whereby said strap means ends can be connected together so as to maintain said rotary grinder means positioned on said straight cradle.

4. A pattern sizing tool as recited in claim 1, wherein the rotary grinder means is arranged to receive, and turn a stem of a dental burr that has a surface that is the milling end; and each holder means is a thin section of metal having a pointed end for supporting the coping positioned thereon, with a rear end of said thin section of material maintained to extend from the positioning means.

5. A pattern sizing tool as recited in claim 4, further including a turret means as the positioning means that is mounted to turn over the second end of the second arm and includes the pair of holder means that each extend at intervals from said turret means, with each said holder means formed to have a pointed end.

6. A pattern sizing tool as recited in claim 5, wherein one of said holder means is a straight section of metal, and the other said holder means is a section of metal that has been bent at a right angle adjacent to its pointed end.

7. A pattern sizing tool as recited in claim 1, wherein the stop means is a bolt means arranged with the second arm to extend therefrom to move its end into alignment for engagement with a plate means that is connected to the first arm, which said bolt means is positionable relative to said second arm such that said bolt means end will contact said plate means to stop movement of the rotary grinder means milling end at a desired distance from one of the holder means ends.

8. A pattern sizing tool as recited in claim 7, wherein the bolt means includes, a threaded body for turning through a compatible threaded hole in said second arm, and an end for manual turning; and further including a scale means arranged with said second arm and adjacent to an indicator means of said bolt means where, turning said bolt means threaded body in said threaded hole moves said indicator means alongside said scale means.

9. A pattern sizing tool comprising a first arm and a second arm, each having first and second ends; pivot means for coupling said first and second arms so as to allow their opposing second ends to be moved apart and together; means for biasing said first and second arms apart; a rotary grinder means and means for maintaining it onto said first arm such that a milling end of said rotary grinder means is positioned apart from said second end of said second arm; a footing means extending from said second end of said second arm opposite to said pivot coupling that is arranged for maintaining a coping thereon to be opposite to and spaced apart from said rotary grinder means milling end; and stop means arranged between said first and second arms for limiting movement together of said rotary grinder means milling end and footing means end, a thumb rest means secured to said second arm that is adjacent to and extends outwardly from said pivot coupling means for receiving an inner surface of a technician's thumb fitted thereto.

\* \* \* \* \*